US008642332B2

(12) United States Patent
Goldman et al.

(10) Patent No.: US 8,642,332 B2
(45) Date of Patent: Feb. 4, 2014

(54) IDENTIFICATION AND ISOLATION OF MULTIPOTENTIAL NEURAL PROGENITOR CELLS FROM THE SUBCORTICAL WHITE MATTER OF THE ADULT HUMAN BRAIN

(75) Inventors: Steven A. Goldman, Webster, NY (US); Neeta Singh Roy, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/793,640

(22) Filed: Mar. 4, 2004

(65) Prior Publication Data

US 2004/0253719 A1 Dec. 16, 2004

Related U.S. Application Data

(60) Provisional application No. 60/453,280, filed on Mar. 7, 2003.

(51) Int. Cl.
C12N 5/074 (2010.01)
C12N 5/079 (2010.01)

(52) U.S. Cl.
USPC .......................................... 435/377; 435/378

(58) Field of Classification Search
USPC .................... 435/368, 377, 378, 384, 325
See application file for complete search history.

(56) References Cited

U.S. PATENT DOCUMENTS

| 4,237,224 | A | | 12/1980 | Cohen et al. |
|---|---|---|---|---|
| 5,491,084 | A | | 2/1996 | Chalfie et al. |
| 5,849,904 | A | * | 12/1998 | Gerardy-Schahn et al. .................. 536/24.31 |
| 6,245,564 | B1 | | 6/2001 | Goldman et al. |
| 2002/0009743 | A1 | * | 1/2002 | Carpenter .................... 435/6 |
| 2003/0040023 | A1 | * | 2/2003 | Klassen et al. .............. 435/7.21 |

FOREIGN PATENT DOCUMENTS

WO WO 01/46384 A2 6/2001

OTHER PUBLICATIONS

Roy et al. Identification, isolation, and promoter-defined separation of mitotic oligodendrocyte progenitor cells from the adult human subcortical white matter. J Neurosci. vol. 19, No. 22, pp. 9986-9995, Nov. 1999.*
Buc-Caron. Neuroepithelial progenitor cells explanted from human fetal brain proliferate and differentiate in vitro. Neurobiol Dis. vol. 2, No. 1, pp. 37-47, Feb. 1995.*
Roy et al. Promoter-targeted selection and isolation of neural progenitor cells from the adult human ventricular zone. J Neurosci Res. vol. 59, No. 3, pp. 321-331, Feb. 2000.*
Mayer-Proschel et al. Isolation of lineage-restricted neuronal precursors from multipotent neuroepithelial stem cells. Neuron. vol. 19, No. 4, pp. 773-785, Oct. 1997.*
Nunes et al. Identification and isolation of multipotential neural progenitor cells from the adult human white matter. Society for Neuroscience Abstracts, vol. 27, No. 1, p. 56, 2001.*
Barres et al. Multiple extracellular signals are required for long-term oligodendrocyte survival. Development. vol. 118, pp. 283-295, 1993.*
Alvarez-Buylla et al., "Neurogenesis in Adult Subventricular Zone," *J. Neurosci.* 22:629-634 (2002).
Barami et al., "Hu Protein as an Early Marker of Neuronal Phenotypic Differentiation by Subependymal Zone Cells of the Adult Songbird Forebrain," *J. Neurobiol.* 28:82-101 (1995).
Barres et al., "A Crucial Role for Neurotrophin-3 in Oligodendrocyte Development," *Nature* 367:371-375 (1994).
Benraiss et al., "Adenoviral Brain-Derived Neurotrophic Factor Induces Both Neostriatal and Olfactory Neuronal Recruitment from Endogenous Progenitor Cells in the Adult Forebrain," *J. Neurosci.* 21:6718-6731 (2001).
Brustle et al., "Chimeric Brains Generated by Intraventricular Transplantation of Fetal Human Brain Cells into Embryonic Rats," *Nat. Biotechnol.* 16:1040-1044 (1998).
Capela et al., "LeX/ssea-1 is Expressed by Adult Mouse CNS Stem Cells, Identifying Them as Nonependymal," *Neuron.* 35:865-875 (2002).
Carpenter et al., "In Vitro Expansion of a Multipotent Population of Human Neural Progenitor Cells," *Exp. Neurol.* 158:265-278 (1999).
Doetsch et al., "Subventricular Zone Astrocytes are Neural Stem Cells in the Adult Mammalian Brain," *Cell* 97:703-716 (1999).
Gleeson et al., "Doublecortin is a Microtubule-Associated Protein and is Expressed Widely by Migrating Neurons," *Neuron.* 23:257-271 (1999).
Gravel et al., "Four-Kilobase Sequence of the Mouse CNP Gene Directs Spatial and Temporal Expression of lacZ in Transgenic Mice," *J. Neurosci. Res.* 53:393-404 (1998).
Han et al., "Transgene Expression in the Guinea Pig Cochlea Mediated by a Lentivirus-Derived Gene Transfer Vector," *Hum. Gene Ther.* 10:1867-1873 (1999).
Jiang et al., "Pluripotency of Mesenchymal Stem Cells Derived from Adult Marrow," *Nature* 418:41-49 (2002).
Johe et al., "Single Factors Direct the Differentiation of Stem Cells from the Fetal and Adult Central Nervous System," *Genes Dev.* 10:3129-3140 (1996).
Kang et al., "Astrocyte-Mediated Potentiation of Inhibitory Synaptic Transmission," *Nat. Neurosci.* 1:683-692 (1998).
Kawaguchi et al., "Nestin-EGFP Transgenic Mice: Visualization of the Self-Renewal and Multiplicity of CNS Stem Cells," *Mol. Cell Neurosci.* 17:259-73 (2001).
Keyoung et al., "High-Yield Selection and Extraction of Two Promoter-Defined Phenotypes of Neural Stem Cells from the Fetal Human Brain," *Nat. Biotech.* 19:843-50 (2001).
Kim et al., Specific Association of Human Telomerase Activity with Immortal Cells and Cancer *Science* 266:2011-2015 (1994).
Kirschenbaum et al., "In Vitro Neuronal Production and Differentiation by Precursor Cells Derived from the Adult Human Forebrain," *Cerebral Cortex* 4(6):576-589 (1994).

(Continued)

Primary Examiner — Jennifer Dunston
(74) *Attorney, Agent, or Firm* — LeClairRyan, a Professional Corporation

(57) ABSTRACT

The present invention is directed to a method of producing neuronal progenitor cells by providing an isolated population of progenitor cells from human brain white matter and permitting the isolated population of cells to differentiate to neuronal progenitor cells. Alternatively, neuronal progenitor cells can be produced by providing an isolated population of glial progenitor cells and permitting the isolated population of glial progenitor cells to differentiate to neuronal progenitor cells.

5 Claims, 8 Drawing Sheets

(56) References Cited

OTHER PUBLICATIONS

Kondo et al., "Oligodendrocyte Precursor Cells Reprogrammed to Become Multipotential CNS Stem Cells," *Science* 289:1754-1757 (2000).

Kukekov et al., "A Nestin-Negative Precursor Cell from the Adult Mouse Brain Gives Rise to Neurons and Glia," *Glia*, 21:399-407 (1997).

Levine et al., "The Oligodendrocyte Precursor Cell in Health and Disease," *Trends Neurosci.* 24:39-47 (2001).

Levy et al., "Retroviral Transfer and Expression of a Humanized, Red-Shifted Green Fluorescent Protein Gene into Human Tumor Cells," *Nat. Biotechnol.* 14:610-614 (1996).

Marusich et al., "Hu Neuronal Proteins are Expressed in Proliferating Neurogenic Cells," *J. Neurobiol.* 25:143-155 (1994).

Mason et al., "A2B5$^+$ and O4$^+$ Cycling Progenitors in the Adult Forebrain White Matter Respond Differentially to PDGF-AA, FGF-2, and IGF-1," *J. Molec. Cell. Neurosci.* 20:30-42 (2002).

Morshead et al., "Neural Stem Cells in the Adult Mammalian Forebrain: A Relatively Quiescent Subpopulation of Subependymal Cells," *Neuron.* 13:1071-1082 (1994).

Nunes et al., "Identification and Isolation of Multipotential Neural Progenitor Cells from the Subcortical White Matter of the Adult Human Brain," *Nat. Med.* 9(4):439-447 (2003).

Ostenfeld et al., "Human Neural Precursor Cells Express Low Levels of Telomerase *in Vitro* and Show Diminishing Cell Proliferation with Extensive Axonal Outgrowth Following Transplantation," *Exp. Neurol.* 164:215-226 (2000).

Palmer et al., "Fibroblast Growth Factor-2 Activates a Latent Neurogenic Program in Neural Stem Cells from Diverse Regions of the Adult CNS," *J. Neurosci.* 19:8487-8497 (1999).

Pincus et al., "Fibroblast Growth Factor-2/Brain-Derived Neurotrophic Factor-Associated Maturation of New Neurons Generated from Adult Human Subependymal Cells," *Ann. Neurol.* 43:576-585 (1998).

Raff et al., "Platelet-Derived Growth Factor from Astrocytes Drives the Clock that Times Oligodendrocyte Development in Culture," *Nature* 333:562-565 (1988).

Reynolds et al., "Generation of Neurons and Astrocytes from Isolated Cells of the Adult Mammalian Central Nervous System," *Science* 255:1707-1710 (1992).

Roy et al., "In Vitro Neurogenesis by Progenitor Cells Isolated from the Adult Human Hippocampus," *Nat. Med.* 6:271-277 (2000).

Sambrook et al., *Molecular Cloning: A Laboratory Manual*, 2nd Edition, Cold Spring Harbor Labortory Press, Cold Spring Harbor, New York (1989) (Table of Contents only).

Sawamoto et al., "Direct Isolation of Committed Neuronal Progenitor Cells from Transgenic Mice Co-Expressing Spectrally-Distinct Fluorescent Proteins Regulated by Stage-Specific Neural Promoters," *J. Neurosci. Res.* 65:220-27 (2001).

Sawamoto et al., "Generation of Dopaminergic Neurons in the Adult Brain from Mesencephalic Precursor Cells Labeled with a Nestin-GFP Transgene," *J. Neurosci.* 21:3895-903 (2001).

Scolding et al., "Oligodendrocyte Progenitors are Present in the Normal Adult Human CNS and in the Lesions of Multiple Sclerosis," *Brain* 121:2221-2228 (1998).

Svendsen et al., "Human Neural Stem Cells: Isolation, Expansion and Transplantation," *Brain Pathol.* 9:499-513 (1999).

Tse et al., "Voltage-Activated K+ Currents in Acutely Isolated Hippocampal Astrocytes," *J. Neurosci.* 12:1781-1788 (1992).

Vescovi et al., "bFGF Regulates the Proliferative Fate of Unipotent (Neuronal) and Bipotent (Neuronal/Astroglial) EGF-Generated CNS Progenitor Cells," *Neuron* 11:951-966 (1993).

Vescovi et al., "Isolation and Cloning of Multipotential Stem Cells from the Embryonic Human CNS and Establishment of Transplantable Human Stem Cells Lines by Epigenetic Stimulation," *Exp. Neurol.* 156:71-83 (1999).

Vicario-Abejon, et al., "Functions of Basic Fibroblast Growth Factor and Neurotrophins in the Differentiation of Hippocampal Neurons," *Neuron.* 15:105-114 (1995).

Wang et al., Isolation of Neuronal Precursors by Sorting Embryonic Forebrain Transfected with GFP Regulated by the T Alpha 1 Tubulin Promoter, *Nat. Biotechnol.* 16:196-201 (1998).

Windrem et al., "Progenitor Cells Derived from the Adult Human Subcortical White Matter Disperse and Differentiate as Oligodendrocytes Within Demyelinated Regions of the Rat Brain," *J. Neurosci. Res.* 69:966-975 (2002).

Yashima et al., "Expression of the RNA Component of Telomerase During Human Development and Differentiation," *Cell Growth Differ.* 9:805-813 (1998).

Zufferey et al., "Woodchuck Hepatitis Virus Posttranscriptional Regulatory Element Enhances Expression of Transgenes Delivered by Retroviral Vectors," *J. Virol.* 73:2886-2892 (1999).

\* cited by examiner

IDENTIFICATION AND ISOLATION OF MULTIPOTENTIAL NEURAL PROGENITOR CELLS FROM THE SUBCORTICAL WHITE MATTER OF THE ADULT HUMAN BRAIN

This application claims the benefit of U.S. Provisional Patent Application Ser. No. 60/453,280, filed Mar. 7, 2003.

This invention was made with government support under grant numbers R01NS39559 and R01NS33106 awarded by The National Institutes of Health. The government has certain rights in this invention.

FIELD OF THE INVENTION

The present invention relates to the identification and isolation of multipotential neural progenitor cells from the subcortical white matter of the adult human brain.

BACKGROUND OF THE INVENTION

The adult human subcortical white matter harbors a population of mitotically-competent oligodendrocyte progenitors, that comprise as many as 3% of its cells (Scolding et al., "Oligodendrocyte Progenitors are Present in the Normal Adult Human CNS and in the Lesions of Multiple Sclerosis [see comments]," *Brain*, 121:2221-2228 (1998); Roy et al., "Identification, Isolation, and Promoter-Defined Separation of Mitotic Oligodendrocyte Progenitor Cells from the Adult Human Subcortical White Matter," *J Neurosci*, 19:9986-9995 (1999)). These cells may be extracted from brain tissue using fluorescence-activated cell sorting (FACS), after transfection with plasmids encoding GFP driven by the promoter for CNP, an early oligodendrocytic transcript (Roy et al., "Identification, Isolation, and Promoter-Defined Separation of Mitotic Oligodendrocyte Progenitor Cells from the Adult Human Subcortical White Matter," *J Neurosci*, 19:9986-9995 (1999); Gravel et al., "Four-Kilobase Sequence of the Mouse CNP Gene Directs Spatial and Temporal Expression of lacZ in Transgenic Mice," *J. Neurosci., Res.* 53:393-404 (1998)). The cells express the immature neural ganglioside recognized by MAb A2B5, but do not express more mature markers of glial lineage. When raised at high density, P/CNP2:hGFP$^+$ progenitors gave rise to glia, largely to oligodendrocytes. Nonetheless, in low density culture following high-purity FACS, P/CNP2:hGFP$^+$ cells often generated βIII-tubulin$^+$ neurons (Roy et al., "Identification, Isolation, and Promoter-Defined Separation of Mitotic Oligodendrocyte Progenitor Cells from the Adult Human Subcortical White Matter," *J Neurosci*, 19:9986-9995 (1999)). Since neurogenesis was essentially never noted from P/CNP2:hGFP$^+$ cells in higher-density or unsorted cultures, it was postulated that the restriction of P/CNP2:hGFP$^+$ progenitor cells to oligodendrocytic phenotype might be an effect of environmental cues, rather than a function of autonomous commitment. As a result, once removed from other cells into high-purity, low-density culture, and hence absent other paracrine or autocrine influences, human subcortical P/CNP2:hGFP$^+$ cells were able to generate neurons as well as glia. Subsequently, Kondo and Raff (Kondo et al., "Oligodendrocyte Precursor Cells Reprogrammed to Become Multipotential CNS Stem Cells," *Science*, 289:1754-1757 (2000)) reported that glial progenitors from the postnatal rat optic nerve could be reprogrammed to generate neurons, following serum or bone morphogenetic protein-induced phenotypic instruction and bFGF-stimulated expansion. Taken together, these findings suggested that glial progenitor cells might retain substantial phenotypic plasticity.

SUMMARY OF THE INVENTION

The present invention is directed to a method of producing neuronal progenitor cells by providing an isolated population of progenitor cells from human brain white matter and permitting the isolated population of cells to differentiate to neuronal progenitor cells.

Another aspect of the present invention is directed to a method of producing neuronal progenitor cells by providing an isolated population of glial progenitor cells and permitting the isolated population of glial progenitor cells to differentiate to neuronal progenitor cells.

BRIEF DESCRIPTION OF THE DRAWINGS

FIGS. 1A and B are FACS graphs showing the extraction of P/CNP2:hGFP$^+$ (FIG. 1A) and A2B5$^+$ white matter progenitor cells (WMPCs) from an adult human white matter dissociate (FIG. 1B). Each plots forward scatter (FCS), a measure of cell size, against fluorescence intensity (Fl-1). When P/CNP2:hGFP and A2B5-based sorts were directly compared, their plots revealed overlapping profiles, but A2B5$^+$ cells were >6-fold more abundant than their P/CNP2:hGFP$^+$ counterparts, reflecting the higher efficiency of A2B5 surface tagging. FIG. 1C-F show progenitors sorted by P/CNP2:hGFP (FIGS. 1C and E) and A2B5 (FIGS. 1D and F) gave rise to O4$^+$ oligodendrocytes. A2B5-based surface antigen sorting may thus be used as a higher-yield alternative to P/CNP2:hGFP transfection-based FACS for isolating WMPCs. Scale: FIGS. 1C-F, 24 μm.

FIG. 2A shows first passage spheres generated from A2B5-sorted cells 2 weeks post-sort. FIG. 2B show first passage spheres arising from P/CNP2:hGFP sorted cells, 2 weeks. FIG. 2C shows second passage spheres derived from an A2B5-sorted sample, at 3 weeks. FIG. 2D shows, once plated onto substrate, the primary spheres differentiated as βIII-tubulin$^+$ neurons, GFAP$^+$ astrocytes and O4$^+$ oligodendrocytes. FIG. 2E shows that neurons, astrocytes, and oligodendrocytes similarly arose from spheres derived from P/CNP2:GFP-sorted WMPCs. FIGS. 2F-H show BrdU incorporation revealed that new neurons (FIG. 2F, βIII-tubulin; FIG. 2G, MAP2), and oligodendrocytes (FIG. 2H, O4) were both generated in vitro. I, βIII-tubulin$^+$ neurons co-expressed neuronal Hu protein (Marusich et al., "Hu Neuronal Proteins are Expressed in Proliferating Neurogenic Cells," *Journal of Neurobiology*, 25:143-155 (1994); Barami et al., "Hu Protein as an Early Marker of Neuronal Phenotypic Differentiation by Subependymal Zone Cells of the Adult Songbird Forebrain," *J Neurobiol*, 28:82-101 (1995), which are hereby incorporated by reference in their entirety). Nuclei counterstained with DAPI. Scale: FIG. 2A-E, 100 μm; FIG. 2F-I, 24 μm.

FIG. 3A-B show secondary spheres subsequently derived from these infections harbored either GFP-tagged (arrowhead) or untagged (arrow) cells, and only less commonly both. FIGS. 3C-D show a GFP$^+$ secondary sphere one week after plating. FIGS. 3E-F show βIII-tubulin$^+$ neurons and GFAP$^+$ astrocytes arising from a single clonally-derived GFP$^+$ secondary sphere. FIG. 3G shows GFP$^+$/O4$^+$ oligodendrocytes arising from a secondary sphere. Scale: FIGS. 3A-B, 100 μm; FIGS. 3C-D, 60 μm; FIGS. 3E-G, 40 μm.

FIGS. 4A-C show that neurons derived from adult human WMPCs expressed a GABAergic phenotype A. The outgrowth of a WMPC-derived neurosphere, stained for neuronal βIII-tubulin after 35 DIV. FIG. 4B shows immunostaining for GAD67 revealed that all 9 neurons in the field were GAD67$^+$, and thus likely GABAergic neurons. FIG. 4C shows DAPI nuclear counrestaining revealed the abundance of cells in the field. FIGS. 4D-F show WMPC-derived neurons developed neuronal Ca$^{2+}$ responses to depolarization. FIG. 4D shows an image of WMPC-derived cells loaded with the calcium indicator dye fluo-3, 10 days after plating of first passage spheres derived from A2B5-sorted white matter (35 DIV total); many fiber-bearing cells of both neuronal and glial morphologies are apparent. FIG. 4E shows the same field after exposure to 100 μM glutamate, and FIG. 4F shows it after exposure to a depolarizing stimulus of 60 mM KCl. The neurons displayed rapid, reversible, >100% elevations in cytosolic calcium in response to K$^+$, consistent with the activity of neuronal voltage-gated calcium channels. Scale=80 μm. FIGS. 4G-H show that a whole cell patch-clamp revealed voltage-gated sodium currents and action potentials in WMPC-derived neurons. FIG. 4G shows a representative cell 14 days after plating of a first passage sphere derived from A2B5-sorted white matter. The cell was patch-clamped in a voltage-clamped configuration, and its responses to current injection recorded. FIG. 4H shows the fast negative deflections noted after current injection that are typical of the voltage-gated sodium currents of mature neurons. Action potentials were noted only at $I_{Na}$>800 pA.

FIG. 5A shows that white matter progenitor cells can generate neurons upon initial isolation. When A2B5 sorted cells were maintained in base media alone or in bFGF-supplemented media, 5-7% βIII-tubulin/TuJ1$^+$ neurons were observed in the culture. WMPC-derived spheres raised continuously in bFGF/NT3/PDGG-AA or sequentially in bFGF/NT3/PDGF-AA, 15% serum/PDGF-AA, and bFGF, gave rise to progressively higher percentages of neurons (see text). *P<0.01, by one-way analysis of variance (ANOVA) with Bonferroni t-test.B. Adult human WMPCs exhibit density-dependent expansion, such that no sphere formation was observed below cell density of 10,000 cells/ml. The incidence of sphere formation was a curvilinear function of cell density ($R^2$=0.9781). FIGS. 5C-D show that only A2B5-selected cells generated spheres. FIG. 5C shows the first passage spheres generated from A2B5$^+$ cells 2 weeks post-sort. FIG. 5D shows the A2B5-depleted remainder of A2B5-cells, derived from the same source culture as FIG. 5C, exhibited no evidence of sphere formation 2 weeks after sort.

FIGS. 6A-B show nestin$^+$ progenitors and doublecortin$^+$ migrants, respectively, each co-expressing human nuclear antigen (hNA) in the hippocampal alvius. FIG. 6C shows CNP$^+$ oligodendrocytes, that were found exclusively in the corpus callosum. FIG. 6D show a low-power image of GFAP$^+$ (stained with anti-human GFAP) astrocytes along the ventricular wall. E, βIII-tubulin$^+$/hNA$^+$ neurons migrating in a chain in the hippocampal alvius. FIG. 6A-E, 40 μm; FIG. 6F-H, 20 μm.

In FIGS. 8A-B, βIII-tubulin$^+$ neurons were observed in the dorsolateral striatum adjacent to the take-off of the rostral migratory stream (RMS) in an E17 transplanted rat. FIG. 8C shows a MAP-2$^+$ neuron in the dorsal striatum; FIG. 8D shows a GAD67$^+$ neuron in the dorsal striatum; FIG. 8E shows a CNP$^+$ oligodendrocyte in the corpus callosum; and FIG. 8F shows a GFAP$^+$ astrocyte in the callosum. Scale: FIG. 8A-F, 14 μm.

DETAILED DESCRIPTION OF THE INVENTION

Figure 1:
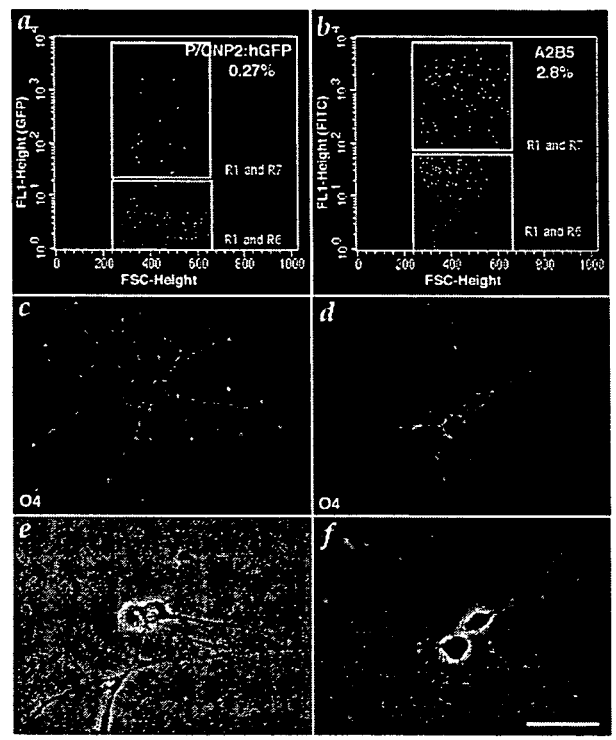
FIG. 1A-F show A2B5-based FACS selects oligodendrocyte progenitor cells.

As used herein, the term "isolated" when used in conjunction with a nucleic acid molecule refers to: 1) a nucleic acid molecule which has been separated from an organism in a substantially purified form (i.e. substantially free of other substances originating from that organism), or 2) a nucleic acid molecule having the same nucleotide sequence but not necessarily separated from the organism (i.e. synthesized or recombinantly produced nucleic acid molecules).

"Enriched" refers to a cell population that is at least 90% pure with respect to the index phenotype, regardless of its initial incidence in the population from which it was derived. "Purified" refers to a cell population at least 99% pure with respect to the index phenotype, regardless of its initial incidence in the reference population.

The present invention is directed to a method of producing neuronal progenitor cells by providing an isolated population of progenitor cells from human brain white matter and permitting the isolated population of cells to differentiate to neuronal progenitor cells.

The step of providing an isolated population of progenitor cells can be carried out using a promoter that functions in the progenitor cells and a nucleic acid encoding a marker protein, as described in U.S. Pat. No. 6,245,564 to Goldman et. al., which is hereby incorporated by reference in its entirety. In particular, this involves providing a mixed population of brain cells which population includes progenitor cells of human white matter and selecting a promoter which functions only in human white matter progenitor cells and not in other cell types. A nucleic acid molecule encoding a marker protein under control of said promoter is introduced into the mixed population of brain cells, and the human white matter progenitor cells, but not the other cell types in the mixed population, are allowed to express the marker protein. The cells expressing the marker protein are identified as being restricted to human white matter progenitor cells and are separated from the mixed population to produce an isolated population of human white matter progenitor cells.

Any promoter which is specific for human white matter can be utilized in this process. "Specific", as used herein to describe a promoter, means that the promoter functions only in the chosen cell type. One suitable promoters is the musashi promoter or the nestin enhancer. See WO 01/46384 to Goldman et al.; Keyoung et al., "Specific Identification, Selection and High-Yield Extraction of Neural Stem Cells from the Fetal Human Brain," *Nature Biotech.* 19:843-50 (2001); Sawamoto et al., "Direct Isolation of Committed Neuronal Progenitor Cells from Transgenic Mice Co-Expressing Spectrally-Distinct Fluorescent Proteins Regulated by Stage-Specific Neural Promoters," *J. Neurosci Res.* 65:220-27 (2001); Kawaguchi et al., "Nestin-EGFP Transgenic Mice: Visualization of the Self-Renewal and Multiplicity of CNS Stem Cells," *Molec. Cell Neurosci.* 17:259-73 (2001); Sawamoto et al., "Generation of Dopaminergic Neurons in the Adult Brain from Mesencephalic Precursor Cells Labeled with a Nestin-GFP Transgene," *J. Neurosci.* 21:3895-903 (2001), which are hereby incorporated by reference in their entirety. Other suitable promoters include the E/nestin enhancer/promoter (Kawaguchi et al., "Nestin-EGFP Transgenic Mice: Visualization of the Self-Renewal and Multiplicity of CNS Stem Cells," Molec. Cell Neurosci. 17:259-73 (2001), which is hereby incorporated by reference in its entirety), the CNP/2 promoter (Roy et al., "Identification, Isolation, and Promoter-Defined Separation of Mitotic Oligodendrocyte Progenitor Cells from the Adult Human Subcortical White Matter," *J Neurosci,* 19:9986-9995 (1999), which is hereby incorporated by reference in its entirety), the GD3 synthase promoter, and the PGDF-alpha receptor promoter.

The marker protein is preferably a green fluorescent protein. The isolated nucleic acid molecule encoding a green fluorescent protein can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the GFP. In one embodiment, the GFP can be from *Aequorea victoria* (U.S. Pat. No. 5,491,084 to Chalfie et al., which are hereby incorporated in their entirety). A plasmid designated pGFP10.1 has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 75547 on Sep. 1, 1993. This plasmid is commercially available from the ATCC and comprises a cDNA which encodes a green fluorescent protein of *Aequorea Victoria* as disclosed in U.S. Pat. No. 5,491,084 to Chalfie et al., which is hereby incorporated in its entirety. A mutated form of this GFP (a red-shifted mutant form) designated pRSGFP-C1 is commercially available from Clontech Laboratories, Inc. (Palo Alto, Calif.).

Mutated forms of GFP that emit more strongly than the native protein, as well as forms of GFP amenable to stable translation in higher vertebrates, are now available and can be used for the same purpose. Alternatively, the GFP can be in humanized form (GFPh) (Levy, J., et al., *Nature Biotechnol.* 14:610-614 (1996), which is hereby incorporated in its entirety). Any nucleic acid molecule encoding a fluorescent form of GFP can be used in accordance with the subject invention.

Other suitable marker proteins include lacZ/beta-galactosidase or alkaline phosphatase.

Standard techniques are then used to place the nucleic acid molecule encoding GFP under the control of the chosen cell specific promoter. Generally, this involves the use of restriction enzymes and ligation.

The resulting construct, which comprises the nucleic acid molecule encoding the GFP under the control of the selected promoter (itself a nucleic acid molecule) (with other suitable regulatory elements if desired), is then introduced into a plurality of cells which are to be sorted. Techniques for introducing the nucleic acid molecules of the construct into the plurality of cells may involve the use of expression vectors which comprise the nucleic acid molecules. These expression vectors (such as plasmids and viruses) can then be used to introduce the nucleic acid molecules into the plurality of cells.

Various methods are known in the art for introducing nucleic acid molecules into host cells. These include: 1) microinjection, in which DNA is injected directly into the nucleus of cells through fine glass needles; 2) dextran incubation, in which DNA is incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell; 3) calcium phosphate coprecipitation, in which cells efficiently take in DNA in the form of a precipitate with calcium phosphate; 4) electroporation, in which cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA); 5) liposomal mediated transformation, in which DNA is incorporated into artificial lipid vesicles, liposomes, which fuse with the cell membrane, delivering their contents directly into the cytoplasm; 6) biolistic transformation, in which DNA is absorbed to the surface of gold particles and fired into cells under high pressure using a ballistic device; and 7) viral-mediated transformation, in which nucleic acid molecules are introduced into cells using viral vectors. Since viral growth depends on the ability to get the viral genome into cells, viruses have devised efficient methods for doing so. These viruses include retroviruses, lentivirus, adenovirus, herpesvirus, and adeno-associated virus.

As indicated, some of these methods of transforming a cell require the use of an intermediate plasmid vector. U.S. Pat. No. 4,237,224 to Cohen and Boyer, which is hereby incorporated in its entirety, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al., *Molecular Cloning: A Laboratory Manual,* 2d Edition, Cold Spring Harbor Laboratory Press, Cold Spring Harbor, N.Y. (1989), which is hereby incorporated in its entirety.

In accordance with one of the above-described methods, the nucleic acid molecule encoding the GFP is thus introduced into a plurality of cells. The promoter which controls expression of the GFP, however, only functions in the cell of interest. Therefore, the GFP is only expressed in the cell of interest. Since GFP is a fluorescent protein, the cells of interest can therefore be identified from among the plurality of cells by the fluorescence of the GFP.

Any suitable means of detecting the fluorescent cells can be used. The cells may be identified using epifluorescence optics, and can be physically picked up and brought together by Laser Tweezers (Cell Robotics Inc., Albuquerque, N. Mex.). They can be separated in bulk through fluorescence activated cell sorting, a method that effectively separates the fluorescent cells from the non-fluorescent cells.

Alternatively, the isolated population of human white matter progenitor cells can be obtained by immunoseparation. Such immunoseparation is carried out by extracting cells expressing immunoreactivity for A2B5, NG2, or anti-GD3 antibodies. It carrying out this procedure, a fluorescently labeled antibody which recognizes an antigen on the human white matter progenitor cells can be used. The fluorescent complex of the labeled antibody attached to the human white matter progenitor cell of interest is the recovered in the matter described above.

The isolated population of progenitor cells are permitted to differentiate to neuronal progenitor cells in the presence of one or more growth factors. These growth factors include basic fibroblast growth factor, platelet-derived growth factor, a neurotrophin-3, or combinations thereof.

After permitting the isolated population of cells to differentiate to neuronal progenitor cells, a purified and enriched population of neuronal progenitor cells is recovered.

This recovery procedure may be carried out by a promoter based separation procedure, as described above, utilizing an enhancer/promoter which functions only in neuronal progenitor cells and not other cell types. A nucleic acid molecule encoding the marker protein under control of the enhancer/promoter is introduced into the cells, and the neuronal progenitor cells are allowed to express the marker protein. The cells expressing the marker protein are separated from the mixed population of cells, where the separated cells are the neuronal progenitor cells.

Alternatively, the recovery procedure can be carried out by immunoseparating the neuronal progenitor cells. Such immunoseparation can be carried out by extracting cells having an polysialylated NCAM antigen. Immunoseparating is carried out with a fluorescently labelled antibody which recognizes an antigen on the neuronal progenitor cells. The fluorescently labeled complex of the labeled antibody and the neuronal progenitor cells can be recovered as described above.

The neuronal progenitor cells are differentiated to neurons. The neurons may be hippocampal neurons, striatal neurons, cortical neurons, or substantia nigral or nigro striatal neurons.

The population of cells used to carry out this method are preferably human cells and can be of adult or fetal origin.

Another aspect of the present invention is directed to a method of producing neuronal progenitor cells by providing an isolated population of glial progenitor cells and permitting the isolated population of glial progenitor cells to differentiate to neuronal progenitor cells.

The step of permitting the isolated population of glial progenitor cells to differentiate to neuronal progenitor cells can be carried out in the presence of one or more growth factors, as described above.

After permitting the isolated population of glial progenitor cells to differentiate to neuronal progenitor cells, a purified and enriched population of neuronal progenitor cells is recovered as described above. The step of recovery can be carried out using promoter-based separation or immunoseparation with a polysialylated NCAM antigen.

The isolated glial progenitor cells may be provided using a promoter-based separation as generally described above. This involves selecting a promoter which functions only in glial progenitor cells and not in the other cell types. A nucleic acid molecule encoding a marker protein under control of said promoter is introduced into all cell types of a mixed population of brain cells. Only the glial progenitor cells, but not the other cell types, within said mixed population are allowed to express said marker protein. The cells of the mixed population that express the marker protein are identified and are restricted to glial progenitor cells. The cells expressing the marker protein are separated from the mixed population to produce an isolated population of glial progenitor cells. In carrying out this procedure, the enhancer/promoter can be an E/nestin enhancer/promoter, a Musashi promoter, a CNP/2 promoter, a GD3 synthase promoter, or a PGDF-alpha receptor promoter. A fluorescent marker protein is used as described above.

Alternatively, the isolated glial progenitor cells may be provided by immunoseparating the glial progenitor cells. In this embodiment of the present invention, immunoseparating is carried out by extracting cells expressing immunoreactivity for A2B5, NG2, or anti-GD3 antibodies. A fluorescently labeled antibody which recognizes an antigen on the glial progenitor cells is used in this procedure.

The glial progenitor cells are preferably human and can be of adult or fetal origin.

Again, after recoverying neuronal progenitor cells starting from an isolated population of glial progenitor cells. The neurons can be hippocampal neurons, striatal neurons, cortical neurons, or substantia nigral or nigro striatal neurons.

EXAMPLES

Example 1

Tissue Dissociation and Culture

Adult subcortical white matter was obtained surgically from 21 patients. These included 14 epileptic resections (age range: 1-50 years; 7 males, 7 females), an aneurysmal repair (69 yr/male), 2 resections of a noncontiguous dysplastic focus (20 yr/male and 36 yr/F), and 4 traumatic temporal lobe decompressions (17-67 yr/all male). Samples were obtained from patients who had consented to tissue use, under protocols approved by the New York Hospital-Cornell and Columbia-Presbyterian Hospital Institutional Review Boards. The samples were dissected and dissociated to single cell suspension using papain/DNAase, as described (Roy et al., "Identification, Isolation, and Promoter-Defined Separation of Mitotic Oligodendrocyte Progenitor Cells from the Adult Human Subcortical White Matter," *J Neurosci,* 19:9986-9995 (1999); Roy et al., "In Vitro Neurogenesis by Progenitor Cells Isolated from the Adult Human Hippocampus," *Nat Med,* 6:271-277 (2000); Roy et al., "Promoter-Targeted Selection and Isolation of Neural Progenitor Cells from the Adult Human Ventricular Zone," *J Neurosci Res,* 59:321-331. (2000), which are hereby incorporated by reference in their entirety). The cells were then suspended in DMEMIF12/N1 with either bFGF (20 ng/ml, Sigma) alone, or bFGF with NT-3 (2 ng/ml, R & D, Inc) and PDGF-AA (20 ng/ml, Sigma), and plated in 100 mm suspension culture dishes (Corning).

Example 2

Magnetic Separation of A2B5$^+$ Cells 24-48 hr after dissociation, the number of viable cells was determined using calcein (Molecular Probes). The cells were then washed and incubated with A2B5 supernatant (clone 105; ATCC, Manassas, Va.) for 30-45 min at 4° C., washed 3× with PBS containing 0.5% bovine serum albumin and 2 mM EDTA, then incubated with microbead-tagged rat anti-mouse IgM (1:4; Miltenyi Biotech), for 30 min at 4° C. The A2B5$^+$ cells were washed, resuspended and separated using positive selection columns, type MS+/RS+ or LS+/VS+ (MACS, Miltenyi Biotech). For flow cytometry of matched samples, cells were incubated in FITC-labeled goat anti-mouse IgM at 1:50 before FACS.

Example 3

Transfection and Sorting

Some samples were transfected with P/CNP2:hGFP after 2-6 DIV, using 2 µg of plasmid DNA and 10 µl of lipofectin, as described (Roy et al., "Identification, Isolation, and Promoter-Defined Separation of Mitotic Oligodendrocyte Progenitor Cells from the Adult Human Subcortical White Matter," *J Neurosci*, 19:9986-9995 (1999); Roy et al., "In Vitro Neurogenesis by Progenitor Cells Isolated from the Adult Human Hippocampus," *Nat Med*, 6:271-277 (2000); Wang et al., "Isolation of Neuronal Precursors by Sorting Embryonic Forebrain Transfected with GFP Regulated by the T Alpha 1 Tubulin Promoter, *Nature Biotechnol*, 16:196-201 (1998), which are hereby incorporated by reference in their entirety). Sorting, both for P/CNP2:hGFP and A2B5-immunofluorescence, was performed on a Becton-Dickinson FACS Vantage, also as described (Roy et al., "Identification, Isolation, and Promoter-Defined Separation of Mitotic Oligodendrocyte Progenitor Cells from the Adult Human Subcortical White Matter," *J Neurosci*, 19:9986-9995 (1999); Roy et al., "In Vitro Neurogenesis by Progenitor Cells Isolated from the Adult Human Hippocampus," *Nat Med*, 6:271-277 (2000); Wang et al., "Isolation of Neuronal Precursors by Sorting Embryonic Forebrain Transfected with GFP Regulated by the T Alpha 1 Tubulin Promoter, *Nature Biotechnol*, 16:196-201 (1998), which are hereby incorporated by reference in their entirety). Untransfected and IgM-exposed control cells were used to calibrate background; a false positive rate of 1% was accepted as cutoff.

Example 4

Generation of Primary and Secondary Spheres

A2B5$^+$ and A2B5-depleted WM cells were distributed to a 24-well plate directly after sorting, at 100,000, 50,000, 25,000, 10,000, 5000, and 1000 cells/ml, in 0.5 ml/well of DMEMIF12/N1 with bFGF/NT3/PDGF-AA. Resultant WMPC-derived neurospheres were passaged at the 50-100 cell stage, by dissociation to single cells by trypsin/EDTA. The cells were plated at 3,000 cells/well. Three weeks later, the resultant secondary spheres were either dissociated and passaged again as tertiary spheres, or plated into 2% FBS with 20 ng/ml BDNF on a polyornithine/fibronectin substrate, and fixed 2 wks later.

Example 5

Lentiviral Tagging and Lineage Analysis

A2B5-sorted cells were infected 2-5 days post-separation with lentivirus (10$^8$ pfu/ml) expressing GFP under CMV promoter control, and a WPRE5 post-transcription regulatory element (Han et al., "Transgene Expression in the Guinea Pig Cochlea Mediated by a Lentivirus-Derived Gene Transfer Vector," *Hum Gene Ther.*, 10:1867-1873 (1999); Zufferey et al., *J. Virology*, 73:2886-2892 (1999), which are hereby incorporated by reference in their entirety). The lentivirus was generated by cotransfecting plasmids pCMV/D R8.91, pMD.G, and pHRCMVGFPwsin into 293T cells, as described (Windrem et al., "Progenitor Cells Derived from the Adult Human Subcortical White Matter Disperse and Differentiate as Oligodendrocytes Within Demyelinated Regions of the Rat Brain," *J. Neurosci. Res.*, 69:966-975 (2002), which is hereby incorporated by reference in its entirety). A2B5-sorted cells were exposed to lentivirus for 24 hrs in polybrene-supplemented media (8 µg/ml), then passaged into fresh media in 24 well plates at a nominal clonal density of 3000 cells/well. GFP expression by tagged cells was observed within 2 days. The primary spheres that arose in these cultures were dissociated 3 weeks later, and replated at 3000 cells/well; secondary spheres arose from these within the 2 weeks thereafter.

Example 6

TRAP Assay

Telomerase activity was determined using the TRAP assay (Ostenfeld et al., "Human Neural Precursor Cells Express Low Levels of Telomerase in Vitro and Show Diminishing Cell Proliferation with Extensive Axonal Outgrowth Following Transplantation," *Exp Neurol*, 164:215-226 (2000); Kim et al., "Specific Association of Human Telomerase Activity with Immortal Cells and Cancer, *Science*, 266:2011-2015 (1994), which are hereby incorporated by reference in their entirety), described in detail in the matter accompanying FIG. 7.

Example 7

In-utero Transplantation

Figure 6:
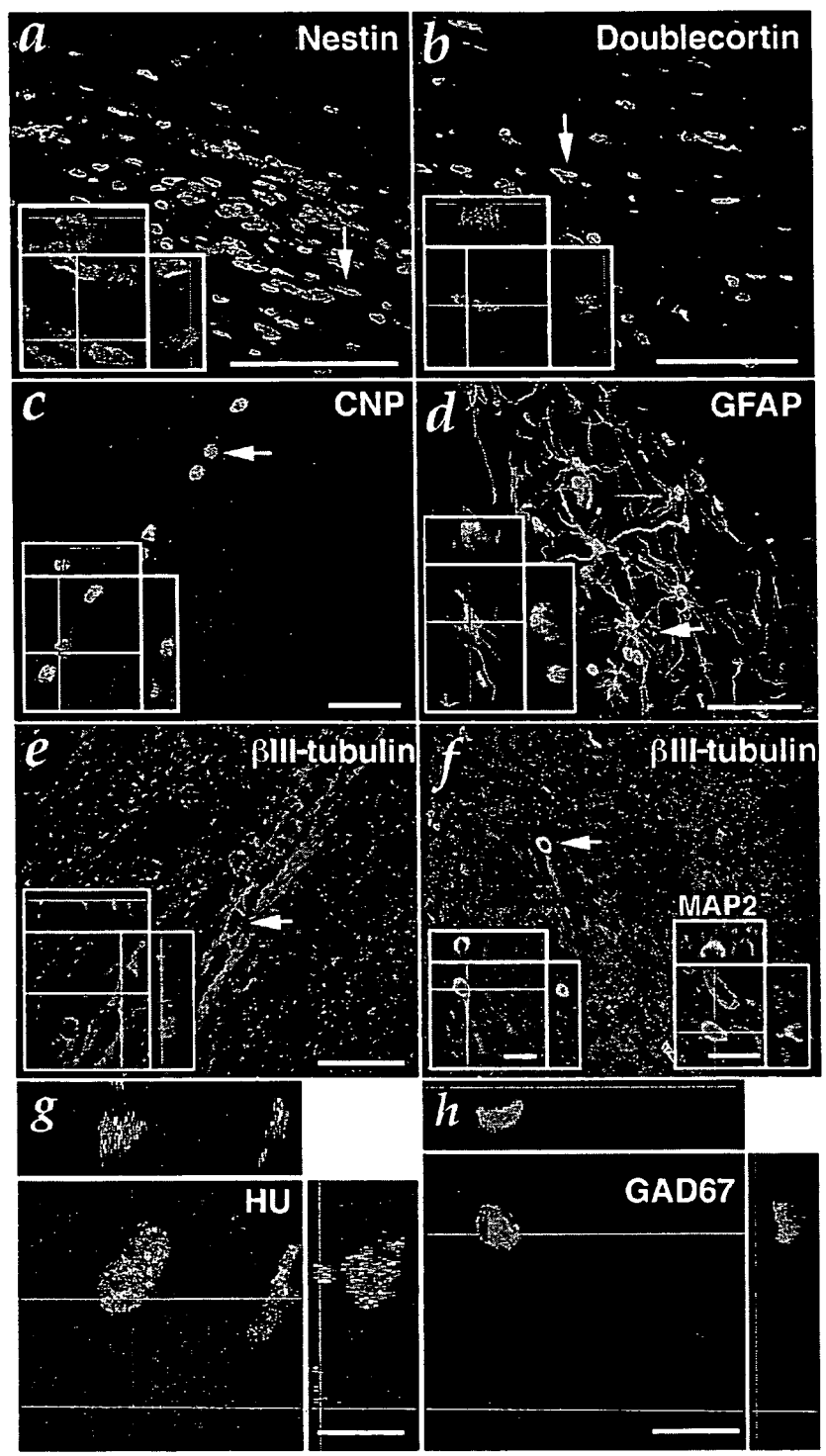
FIGS. 6A-E show WMPCs engrafted into fetal rats gave rise to neurons and glia in a site-specific manner. Sections from a rat brain were implanted at E17 with A2B5-sorted WMPCs and sacrificed a month after birth. These cells were maintained in culture for 10 days prior to implant.
FIG. 6F shows βIII-tubulin$^+$ and MAP2$^+$ (inset in FIG. 6F) neurons in the striatum, adjacent to the RMS (antigens; hNA; double-stained human nuclei).
FIG. 6G shows an Hu$^+$/hNA$^+$ neuron in the septum.
FIG. 6H shows an hNA$^+$/GAD-67$^+$ striatal neuron. Insets in each figure show orthogonal projections of a high power confocal image of the identified cell (arrow). Scale.
Figure 8:
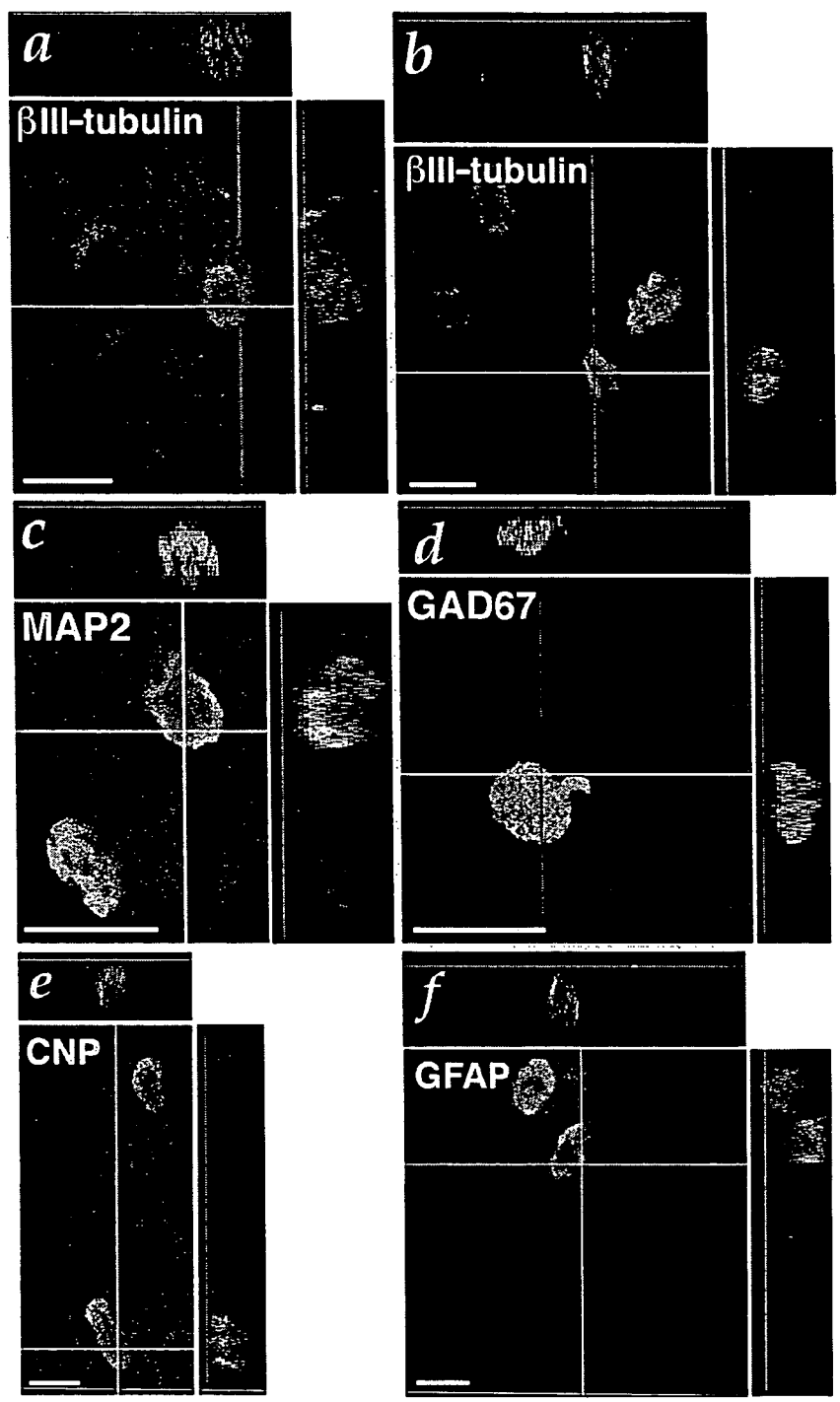
FIGS. 8A-F show acutely sorted-human WMPCs engrafted into fetal rats gave rise to neurons and glia. Rats implanted at E17 with A2B5-sorted WMPCs were sacrificed a month after birth and their brains were sectioned and immunostained first with anti-human nuclear antigen antibody (hNA) to localize the transplanted cells.

Transuterine xenograft into E17 rat fetuses was performed as described (Keyoung et al., "Specific Identification, Selection and Extraction of Neural Stem Cells from the Fetal Human Brain," *Nature Biotechnology*, 19:843-850 (2001); Brustle et al., "Chimeric Brains Generated by Intraventricular Transplantation of Fetal Human Brain Cells into Embryonic Rats," *Nat Biotechnol*, 16:1040-1044 (1998), which are hereby incorporated by reference in their entirety). Some cells were injected within 24-48 hrs after sorting and others after 10 days in vitro in FGF2/PDGF-AA/NT-3. This yielded 2 sets of animals, that included: 1) acutely isolated WMPCs injected on E17 (FIG. 8) and 2) neurosphere-expanded WMPCs injected on E17 (FIG. 6). A month after implantation, the animals were perfusion-fixed by 4% paraformaldehyde. Experiments were conducted with the approval of the Institutional Animal Care and Use Committee of the Weill Medical College of Cornell University.

Example 8

Immunocytochemistry

Xenografted rat brains were cryosectioned at 15 µm, then permeabilized with PBS/0.1% saponin/1% NGS, and blocked with PBS/0.05% saponin/5% NGS, each for 30 min. Sections were labeled with mouse anti-human nuclear antigen (hNA, 1:50, Chemicon, Temecula, Calif.), then immunostained for either: βIII-tubulin (TuJ1, 1:600, Covance), MAP2 (AP-20, 1:50, Sigma), Hu (mouse anti-HuC/HuD Mab 16A11, 25 µg/ml; Dr. H. Fumeaux), GAD67 (rabbit-anti GAD67, 1:100, Chemicon), GFAP (mouse anti-GFAP, 1:1000, SMI 21, Stemberger; or rabbit anti-GFAP, 1:400, Sigma), CNP (mouse anti-CNP, 1:1000, SMI 91), human nestin (rabbit anti-nestin, 1:200, Chemicon), or doublecortin (rabbit antisera, 1:100, Dr. C. Walsh). The sections were incubated with antibody overnight at 4° C. Species and isotype-specific fluorescent secondary antibodies were applied at 1:100, for 1.5 hrs at RT.

In vitro, O4 and A2B5 were immunolabeled as described (Roy et al., "Identification, Isolation, and Promoter-Defined Separation of Mitotic Oligodendrocyte Progenitor Cells from the Adult Human Subcortical White Matter," *J Neurosci*, 19:9986-9995 (1999), which is hereby incorporated by reference in its entirety). For multiple antigen labeling, O4 was localized on live cells, which were then fixed and stained for βIII-tubulin, MAP2, GFAP, Hu, GAD67, or BrdU. O4 supernatant (Drs. R. Bansal and S. Pfeiffer) was used at 1:100 for 40 min at 4° C. Antibodies against βIII-tubulin, MAP-2, GFAP and BrdU (rat anti-BrdU, Harlan; 1:200) were incubated overnight at 4° C. Fixed cultures were counterstained with DAPI (10 µg/ml; Molecular Probes, Eugene, Oreg.).

Example 9

Confocal Imaging

In the xenografted brains, single cells that appeared co-labeled for both human- and cell specific markers were evaluated by confocal imaging, as describe (Keyoung et al., "Specific Identification, Selection and Extraction of Neural Stem Cells from the Fetal Human Brain," *Nature Biotechnology*, 19:843-850 (2001); Benraiss et al., "Adenoviral BDNF Induces Both Neostriatal and Olfactory Neuronal Recruitment from Endogenous Progenitor Cells in the Adult Forebrain," *J. Neuroscience*," 21:6718-6731 (2001), which are hereby incorporated by reference in their entirety). To be deemed double-labeled, cells were required to have anti-human nuclear antigen signal surrounded by neuronal or glial immunoreactivity in every serially acquired 0.4 µm z-dimension optical section, as well as in each orthogonal side-view thereof.

Example 10

Calcium Imaging

Outgrowths from both first and second passage WMPC-derived neurospheres were assessed 2-3 weeks after plating into BDNF-supplemented DMEMIF12/N1 with 2% FBS. These mixed neuronal and glial outgrowths were challenged with 100 µM glutamate or 60 mM $K^+$, during which their cytosolic calcium levels were observed. Calcium imaging was performed using confocal microscopy of cultures loaded with fluo-3 acetoxymethylester (Molecular Probes, OR) (Roy et al., "In Vitro Neurogenesis by Progenitor Cells Isolated from the Adult Human Hippocampus," *Nat Med*, 6:271-277 (2000); Kirschenbaum et al., "In Vitro Neuronal Production and Differentiation by Precursor Cells Derived from the Adult Human Forebrain," *Cerebral Cortex*, 4:576-589 (1994); Pincus et al., "FGF2/BDNF-Associated Maturation of New Neurons Generated from Adult Human Subependymal Cells," *Ann. Neurology*, 43:576-585 (1998), which are hereby incorporated by reference in their entirety). It was previously reported that adult progenitor-derived human neurons displayed a mean calcium rise of >400% to 60 mM $K^+$ in vitro; this compared to glial responses of <20% (Pincus et al., "FGF2/BDNF-Associated Maturation of New Neurons Generated from Adult Human Subependymal Cells," *Ann. Neurology*, 43:576-585 (1998), which is hereby incorporated by reference in its entirety). In this study, neuronal identity was assigned to cells exhibiting ≥2-fold calcium increments to depolarization.

Example 11

Electrophysiology

Sister cultures to those subjected to calcium imaging were also assessed by whole-cell patch clamp analysis. Whole-cell voltage-clamped recordings of fiber-bearing cells were performed and analyzed as described (Kang et al., "Astrocyte-Mediated Potentiation of Inhibitory Synaptic Transmission," *Nat Neurosci*, 1:683-692 (1998); Roy et al., "In Vitro Neurogenesis by Progenitor Cells Isolated from the Adult Human Hippocampus," *Nat Med*, 6:271-277 (2000), which are hereby incorporated by reference in their entirety). A holding potential of −60 mV and voltage steps of 10 mV with 100 ms durations were applied to the recorded cells through the patch electrodes. Signals were sampled every 50 µs.

Example 12

WMPCs were Isolated by P/CNP2:GFP and A2B5-based Sorting

White matter was dissected from surgical samples taken at the time of temporal lobectomy for epilepsy, aneurysm, and post-traumatic decompression (n=21). The tissues were dissected free of adjacent cortex and ventricular epithelium, and enzymatically dissociated to single cell suspension, as described (Roy et al., "Identification, Isolation, and Promoter-Defined Separation of Mitotic Oligodendrocyte Progenitor Cells from the Adult Human Subcortical White Matter," *J Neurosci*, 19:9986-9995 (1999), which is hereby incorporated by reference in its entirety). The dissociates were plated onto laminin (100 µg/ml) in DMEM/F12/N1 supplemented with bFGF (20 ng/ml), NT3 (2 ng/ml), and PDGF-AA (20 ng/ml). To identify oligodendrocyte progenitors, the dissociates were transfected with P/CNP2:hGFP, the transcription of which results in GFP expression by oligodendrocyte progenitor cells (Roy et al., "Identification, Isolation, and Promoter-Defined Separation of Mitotic Oligodendrocyte Progenitor Cells from the Adult Human Subcortical White Matter," *J Neurosci*, 19:9986-9995 (1999), which is hereby incorporated by reference in its entirety).

To avoid both the temporal lag between transfection and GFP expression and the inefficiency of plasmid transfection, cultures were also sorted on the basis of A2B5 surface immunoreactivity, which can serve as a surrogate marker for P/CNP2:hGFP$^+$ WMPCs in vitro (Roy et al., "Identification, Isolation, and Promoter-Defined Separation of Mitotic Oligodendrocyte Progenitor Cells from the Adult Human Subcortical White Matter," *J Neurosci*, 19:9986-9995 (1999), which is hereby incorporated by reference in its entirety). Indeed, immunostaining revealed that 84±8.3% of P/CNP2: GFP$^+$ cells expressed A2B5 (Roy et al., "Identification, Isolation, and Promoter-Defined Separation of Mitotic Oligodendrocyte Progenitor Cells from the Adult Human Subcortical White Matter," *J Neurosci*, 19:9986-9995 (1999), which is hereby incorporated by reference in its entirety). FACS based on GFP gated 0.49±0.15% of all white matter cells as CNP2:hGFP$^+$ (mean±SE; n=3 patients) (FIG. 1A). Matched cultures transfected with P/CMV:GFP exhibited a net transfection efficiency of 13.1%. Thus, the predicted incidence of P/CNP2:hGFP-defined cells in the white matter was 3.7% (=1/0.131×0.49), consistent with prior estimates of the incidence of this phenotype[2]. From these same samples, A2B5-based FACS gated an average of 3.1±0.7% (n=3) of the WM cell population (FIG. 1B). The >6-fold increase in net yield accruing to the use of A2B5 (3.1% vs. 0.49%) reflected the higher efficiency of A2B5 immunodetection relative to P/CNP2:hGFP plasmid transfection. On this basis, immunomagnetic sorting (IMS) was used to select A2B5$^+$ cells from adult WM dissociates. By IMS, the incidence of A2B5-sorted cells in white matter dissociates was 3.6±0.3% (n=21), and the median 3.1%. This improved yield was accomplished with no appreciable loss of cell-type specificity, in that the A2B5$^+$ cells overlapped entirely the sort profiles of P/CNP2: hGFP$^+$ cells, and each isolate generated O4$^+$ oligodendrocytes with similar efficiency (FIGS. 1C-F). Thus, A2B5-based FACS and IMS identified WMPCs homologous to those recognized by P/CNP2:GFP-based FACS, while permitting the higher-yield isolation of these cells.

Example 13

Adult Human WMPCs Gave Rise to Multipotent Neurospheres

Figure 2:
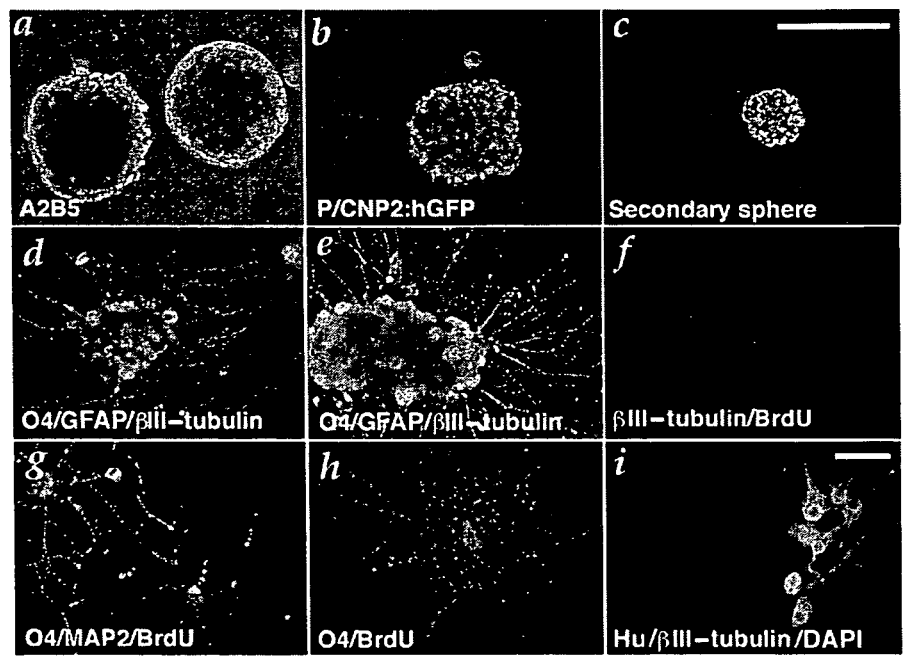
FIGS. 2A-I show adult human WMPCs give rise to multipotential neurospheres.

To assess the expansion capacity of P/CNP2:hGFP and A2B5 sorted cells, sorted isolates of each were propagated in suspension (Reynolds et al., "Generation of Neurons and Astrocytes from Isolated Cells of the Adult Mammalian Central Nervous System," *Science*, 255:1707-1710 (1992); Morshead et al., "Neural Stem Cells in the Adult Mammalian Forebrain: A Relatively Quiescent Subpopulation of Subependymal Cells," *Neuron*, 13:1071-1082 (1994), which are hereby incorporated by reference in their entirety). The cells were distributed into 24-well plates at 50,000/0.5 ml, in serum-free media (SFM) supplemented with bFGF (20-ng/ml), NT-3 (2 ng/ml), and PDGF-AA (20 ng/ml), the combination of which permits the expansion of human WMPCs (Roy et al., "Identification, Isolation, and Promoter-Defined Separation of Mitotic Oligodendrocyte Progenitor Cells from the Adult Human Subcortical White Matter," *J Neurosci*, 19:9986-9995 (1999), which is hereby incorporated by reference in its entirety). Seven days later, the cells were switched to SFM with bFGF alone (20 ng/ml) (Palmer et al., "Fibroblast Growth Factor-2 Activates a Latent Neurogenic Program in Neural Stem Cells from Diverse Regions of the Adult CNS," *J Neurosci*, 19:8487-8497 (1999), which are hereby incorporated by reference in their entirety). Over the ensuing 10 days, neurospheres—i.e. spherical masses of cells that expand from single parental progenitors—arose in these cultures, such that by 3 weeks post-sort, there were 84.8±9.0 spheres/well (n=4 patients); these were typically >150 µm in diameter, and included 46.5±8.2 cells per sphere (FIGS. 2A-B). Thus, single WMPCs of the adult human brain were capable of generating neurospheres.

To establish the lineage potential of single adult human WMPCs, the resultant primary neurospheres were next lineage dissociated and passaged into new wells. Alternatively, some were plated onto substrate to permit their differentiation. Immunostaining revealed that both P/CNP2:hGFP and A2B5$^+$ progenitor-derived spheres gave rise to all major neural phenotypes (FIG. 2D). Among those cells passaged from primary spheres, secondary spheres were observed to arise within 2 weeks after passage. After expansion, these secondary spheres were similarly plated on substrate, then raised for 1-2 weeks and fixed. Immunolabeling confirmed that virtually all secondary spheres generated both neurons and glia together (FIGS. 2C and 2E). In addition, when the mitotic marker BrdU was added to A2B5-sorted cells, BrdU-incorporating neurons, oligodendrocytes and astrocytes were all noted to emerge from the spheres thereby generated (FIGS. 2F-2I). The persistence of mitotic neurogenesis and gliogenesis by single spheres suggested the residence therein of cycling multipotential cells. Moreover, the secondary spheres were likely of clonal origin, given the low plating density of the single cells from which each derived, and the origin of these sphere-forming cells from primary spheres that themselves expanded from nominally single cell dissociates. Together, these data suggested that single progenitor cells of the adult human WM are both clonogenic and multipotential.

Example 14

Single WMPCs Remained Multipotential with Passage

Figure 3:
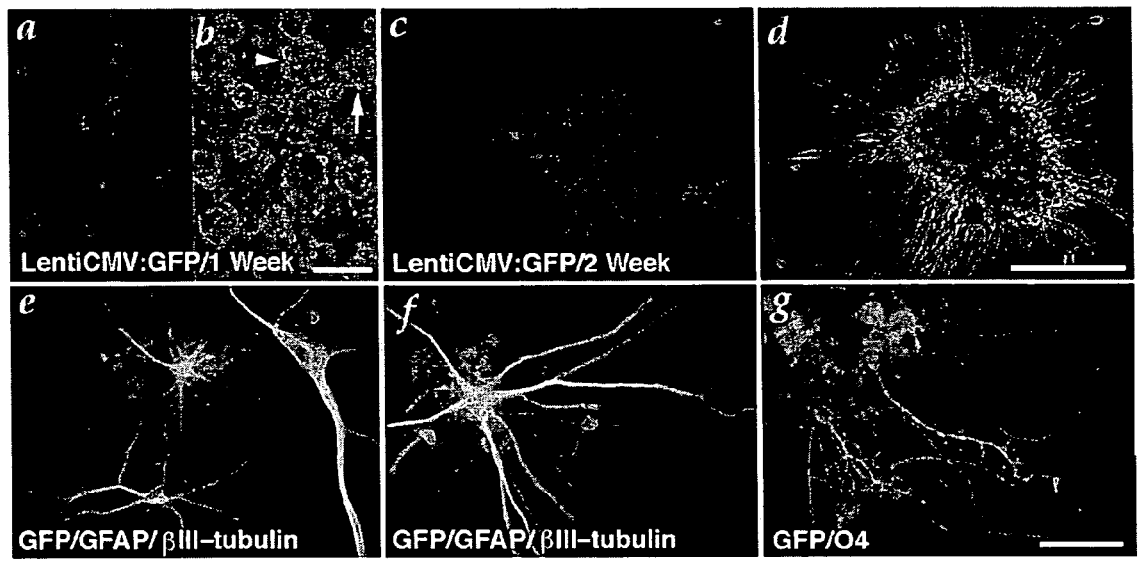
FIG. 3A-G show single lentiviral GFP-tagged WMPCs generated neurons and glia. A2B5-sorted WMPCs were infected with a lentivirus encoding EGFP (Windrem et al., "Progenitor Cells Derived from the Adult Human Subcortical White Matter Disperse and Differentiate as Oligodendrocytes Within Demyelinated Regions of the Rat Brain," *J. Neurosci. Res.*, 69:966-975 (2002), which is hereby incorporated by reference in its entirety), 5 days post-sort.

The serial propagability of sorted WMPCs from neurospheres arising in low-density dissociates suggested the clonal derivation of each individual sphere (Vescovi et al., "Isolation and Cloning of Multipotential Stem Cells from the Embryonic Human CNS and Establishment of Transplantable Human Stem Cells Lines by Epigenetic Stimulation," *Exp. Neurol.*, 156:71-83 (1999); Svendsen et al., "Human Neural Stem Cells: Isolation, Expansion and Transplantation," *Brain Pathol.*, 9:499-513 (1999); Carpenter et al., "In Vitro Expansion of a Multipotent Population of Human Neural Progenitor Cells," *Exp. Neurol.*, 158:265-278 (1999), which are hereby incorporated by reference in their entirety). To further validate the clonal origin of neurons and glia arising within single spheres, lentiviral GFP was next used to genetically tag and follow single WMPCs. To this end, A2B5$^+$ cells were tagged 2-5 days after sorting with a lentivirus expressing GFP under CMV promoter control (Han et al., "Transgene Expression in the Guinea Pig Cochlea Mediated by a Lentivirus-Derived Gene Transfer Vector," *Hum Gene Ther.*, 10:1867-1873 (1999); Zufferey et al., *J. Virology*, 73:2886-2892 (1999); Windrem et al., "Progenitor Cells Derived from the Adult Human Subcortical White Matter Disperse and Differentiate as Oligodendrocytes Within Demyelinated Regions of the Rat Brain," *J. Neurosci. Res.*, 69:966-975 (2002), which are hereby incorporated by reference in their entirety). At 10 pfu/cell, 23% of the cells expressed GFP by 1 week after sorting, yielding a mixture of GFP$^-$, GFP$^+$, and mixed spheres in the resultant cultures (FIGS. 3A-3B). These primary spheres were triturated 2-4 weeks later to single cell suspension, then passaged into bFGF at approximately 3000 cells/well. Under these conditions, 40.8±12.9 secondary spheres/well were generated, indicating a clonogenic cell incidence of 1.3% (n=5). Of these secondary spheres, 47.2±10.8% contained only GFP$^+$ cells (e.g., FIGS. 3C-3D), while 30.9±6.9% harbored no GFP$^+$ cells. The relative uniformity of GFP expression—or lack thereof—among the cells within a given sphere argued that most spheres were clonally-derived (P<0.005 by $X^2$ analysis. This tested the null hypothesis that the spheres arose from the non-clonal aggregation of two or more cells, each of which was equally likely to be GFP$^+$ or GFP$^-$). When the single spheres were plated onto polyornithine/fibronectin and their outgrowth assessed 2 weeks later, all were found to give rise to both neurons and glia (FIGS. 3E-G). Since most secondary spheres were likely to have been clonally-derived and all included neurons as well as glia (38/38 spheres, n=4 samples), then single WMPCs must have given rise to neurons and glia together.

Figure 4:
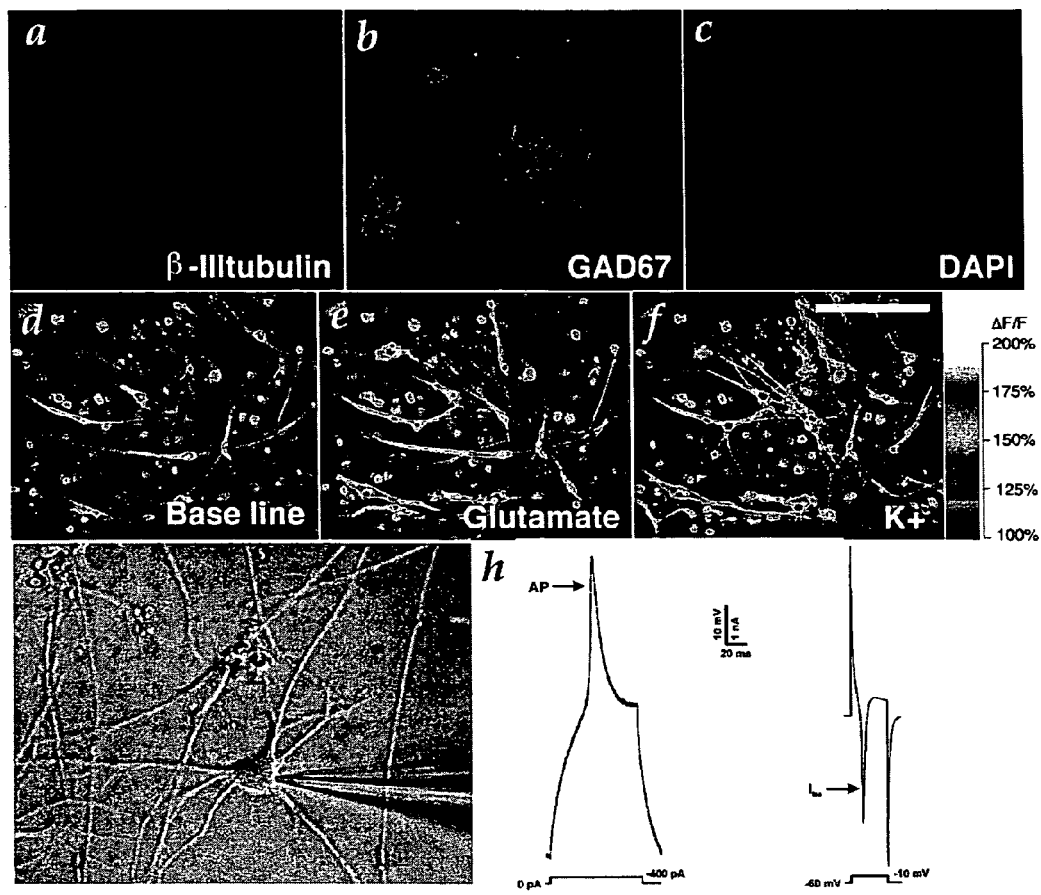
FIGS. 4A-H show WMPC-derived neurons exhibited functional maturation in vitro.

It was next asked if the neurogenic capacity and multilineage competence of WMPCs were maintained with passage. Primary spheres were raised serially in bFGF/NT3/PDGF-AA (7 d), DMEM/F12/N1 with 15% serum/PDGF-AA (4 d), and serum-free DMEM/F12/N1 with bFGF (10 d), then dissociated and replated in bFGF at 3000 cells/well in a 24 well plate. Secondary spheres arose within 2 weeks from 1.1±0.3% of these cells (n=8). After ≥2 weeks of further expansion, the secondary spheres were plated on polyornithine/fibronectin, and 2 weeks later fixed and immunostained (7-9 weeks post-sort). Whereas primary spheres consisted of 21.7±4.3% βIII-tubulin$^+$ neurons, 17.7±3.9% GFAP$^+$ astrocytes, and 46.7±5.9% O4$^+$ oligodendrocytes (n=3), secondary spheres consisted of 16.0±2.5% neurons, 19.3±3.2% astrocytes, and 46.4±2.4% oligodendrocytes (n=3). Most of the neurons were GABAergic, by virtue of their expression of glutamic acid decarboxylase-67 (GAD67) (FIGS. 4A-4C). Since the relative proportions of neurons, oligodendrocytes, and astrocytes in secondary spheres were similar to those of primary spheres, it was concluded that WMPCs retained multilineage competence with expansion.

Example 15

WMPC-derived Neurons Became Functionally Mature

To establish the ability of WMPC-derived neurons to respond in a mature fashion to depolarizing stimuli, they were assessed for both their calcium responses and membrane currents to depolarizing stimuli. Primary spheres (n=12 fields, derived from 3 brains) were plated on fibronectin to permit neuronal outgrowth, and 14 days later assessed for their calcium responses to depolarizing stimuli. The cultures were loaded at that point with the calcium indicator dye fluo-3, and serially exposed to both 100 µM glutamate and 60 mM K$^+$ during confocal microscopy. Astrocytic responses to depolarization were minimal under these culture conditions, as previously noted. In contrast, neuron-like cells displayed rapid, reversible, >100% elevations in cytosolic calcium in response to K$^+$, consistent with the activity of neuronal voltage-gated calcium channels (FIGS. 4D-4F). The neuronal phenotype of these cells was then validated by immunostaining for βIII-tubulin.

It was next asked whether WMPC-derived neurons were able to develop the fast sodium currents and action potentials characteristic of electrophysiologically-competent neurons. For this purpose, whole-cell patch clamp recording was used during current stimulation to assess the response characteristics of WMPC-derived neurons, that arose from plated secondary spheres derived from A2B5-sorted isolates. A total of 58 WMPC-derived fiber-bearing cells were recorded, in 5 cultures derived from 3 patients. Of these 13 exhibited voltage-activated Na$^+$ currents ($I_{Na}$) of >100 nA, and 7 had $I_{Na}$>600, compatible with the fast sodium currents of neuronal depolarization (Kang et al., "Astrocyte-Mediated Potentiation of Inhibitory Synaptic Transmission," Nat Neurosci, 1:683-692 (1998); Tse et al., "Voltage-Activated K+ Currents in Acutely Isolated Hippocampal Astrocytes," J Neuroscience, 12:1781-1788 (1992), which are hereby incorporated by reference in their entirety). Accordingly, whereas 2 of 5 cells with $I_{Na}$>800 generated stimulus-evoked action potentials (FIGS. 4G-4H), none did so with $I_{Na}$<800. In addition, none of 26 morphologically non-neuronal cells displayed significant (≥100 pA) current-induced sodium current. Together, these results indicated that neurons arising from adult human WMPCs developed mature electrophysiologic functions, including both fast sodium currents and action potentials.

Example 16

WMPCs Generated Neurons without Extensive Reprogramming

Glial progenitor cells from the postnatal rat optic nerve can generate neurons, under conditions that Kondo et al. have described as "reprogramming" glial progenitors to multilineage competence (Kondo et al., "Oligodendrocyte Precursor Cells Reprogrammed to Become Multipotential CNS Stem Cells," Science, 289:1754-1757 (2000), which is hereby incorporated by reference in its entirety). In that study, neurogenesis was achieved by first instructing the cells to an intermediary astrocytic lineage, using either serum or bone morphogenetic protein-2, followed by bFGF-stimulated mitogenesis. It was, therefore, asked whether such reprogramming steps are required for the generation of neurons from adult human WMPCs, or whether instead simple expansion under minimal conditions in vitro, with the removal of these cells from their environment, might be sufficient to permit neurogenesis by these cells. To this end, sorted A2B5$^+$ cells were cultured in several permutations of mitogenic and differentiative conditions, so as to identify minimal conditions permissive for lineage diversification. The phenotypes generated were compared to these conditions:

1) bFGF/NT3/PDGF-AA in serum-free basal media (SFM, composed of DMEM/F12/N1) for 7 days, followed by 15% FBS/PDGF-AA-supplemented media for 4 days, and SFM with bFGF for 2 weeks;

2) bFGF/NT3/PDGF-AA in SFM, continuously for 3 weeks; and, 3) bFGF alone in SFM, for 3 weeks.

The first condition was intended to promote initial differentiation in serum, while the latter two groups were designed to skip this glial differentiative step (Kondo et al., "Oligodendrocyte Precursor Cells Reprogrammed to Become Multipotential CNS Stem Cells," Science, 289:1754-1757 (2000), which is hereby incorporated by reference in its entirety).

Figure 5:
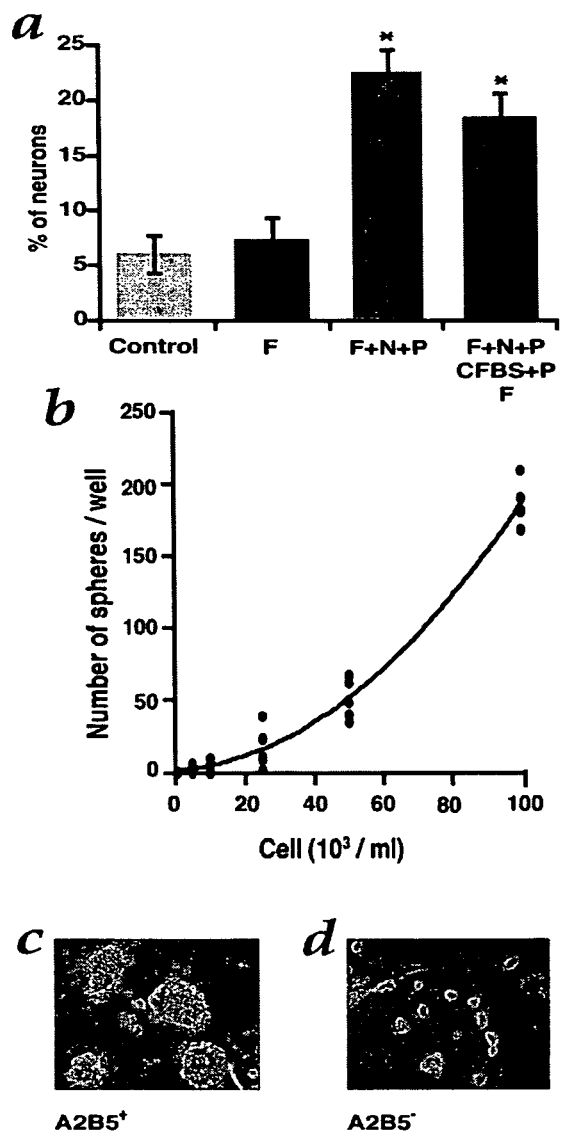
FIGS. 5A-D show WMPCs exhibit both density-dependent expansion and neurogenesis.

The A2B5-sorted progenitors yielded spheres in each of these conditions; however, both the number of spheres, and the percentage of neurons generated by each, differed as a function of treatment. Cultures maintained in base media alone, or in bFGF-supplemented media, exhibited 5.9±1.7% and 7.2±2.1% βIII-tubulin$^+$ neurons, respectively (n=3 patients). When matched WMPC-derived spheres were sequentially raised in bFGF/NT3/PDGF-AA, 15% serum and bFGF, 18.2±2.2% of the cells were βIII-tubulin$^+$ (FIG. 5A). Yet a similar proportion of neurons (22.5±1.9%; n=3) was generated by those neurospheres maintained in SFM with bFGF/NT3/PDGF-AA. Serum exposure was, therefore, not required for A2B5$^+$ cells to generate neurons. Indeed, no specific signals seemed necessary for neuronal instruction besides those provided by PDGF and NT3. These data suggested that antecedent astrocytic differentiation was not a necessary prerequisite to neurogenesis by adult WMPCs. To the contrary, these cells required neither prolonged mitogenic expansion, nor specific dedifferentiation steps, in order to generate neurons as well as glia (Kondo et al., "Oligodendrocyte Precursor Cells Reprogrammed to Become Multipotential CNS Stem Cells," Science, 289:1754-1757 (2000), which is hereby incorporated by reference in its entirety).

Of note, although both PDGF and NT3 have been found to promote oligodendrocyte production by glial progenitors of the rat optic nerve (Barres et al., "A Crucial Role for Neurotrophin-3 in Oligodendrocyte Development," Nature, 367: 371-375 (1994); Raff et al., "Platelet-Derived Growth Factor from Astrocytes Drives the Clock that Times Oligodendrocyte Development in Culture," Nature, 333:562-565 (1988). Raff et al., "Platelet-Derived Growth Factor from Astrocytes Drives the Clock that Times Oligodendrocyte Development in Culture," Nature, 333:562-565 (1988), which are hereby incorporated by reference in its entirety), each has been shown to induce neuronal differentiation in less-committed hippocampal and ventricular zone neural progenitors (Vicario-Abejon, et al., "Functions of Basic Fibroblast Growth Factor and Neurotrophins in the Differentiation of Hippocampal Neurons," Neuron, 15:105-114 (1995); Johe et al., "Single Factors Direct the Differentiation of Stem Cells from the Fetal and Adult Central Nervous System," Genes Dev, 10:3129-3140 (1996), which are hereby incorporated by reference in their entirety). As such, their neurogenic effects on adult WMPCs may reflect the relatively undifferentiated state of these cells.

Example 17

Clonogenic Cells Comprised a Fraction of A2B5+ Cells

It was next sought to assess the incidence of clonogenic and multipotential progenitor cells within the larger pool of A2B5-sorted white matter cells. It was first asked whether either the survival or mitotic competence of adult human WMPCs were density-dependent, by assessing the limiting dilution at which clonogenic progenitors could be obtained from A2B5-sorted white matter dissociates. To this end, A2B5+ cells were plated immediately after sorting, at densities of 100,000, 50,000, 25,000, 10,000, 5000, and 1000 cells/ml (0.5 ml cell suspension/well of a 24 well plate), in basal media supplemented with bFGF/NT-3/PDGF-AA. Under these conditions, the incidence of clonogenic progenitors was a curvilinear function of the sorted cell density ($R^2=0.978$; FIG. 5B). Thus, whereas 186±7.6 spheres were generated at density of 100,000 cells/ml (0.4%; n=5 patients), only 6.5±2.7 were noted at 10,000 cells/ml (0.1%), and no sphere generation whatsoever was noted at or below 5000/ml. Thus, the expansion of purified WMPCs was density-dependent, and optimal at 50,000-100,000 cells/ml. Densities higher than that appeared to promote the terminal differentiation of the progenitors.

To assess whether clonogenic WMPCs were restricted to the A2B5+ population, the A2B5-depleted pool remaining from each sort was also cultured. It was found that at no cell density assessed, over the range of 1000-100,000 cells/ml, did A2B5-depleted cultures give rise to any passageable neurospheres (FIG. 5C). It was concluded on the basis of these studies that whereas only a fraction of white matter A2B5+ cells are actually clonogenic and multipotential progenitors, all clonogenic WMPCs are A2B5+.

Example 18

Adult WMPCs Exhibited Limited Self-Renewal

It was next sought to define the extent to which WMPCs were self-renewing. To this end, the extent to which WMPC-derived neurospheres were capable of repetitive passage was assessed. Primary spheres were raised from 3 patients, at an optimal initial density (100,000 cells/ml), using those conditions identified as most supportive of multilineage expansion (bFGF/NT-3/PDGF-AA in DMEM/F12/N1). A month later, the spheres were dissociated and replated. Secondary spheres were generated, which a month later were replated at $1-5 \times 10^4$ cells/ml; these cultures gave rise to tertiary spheres over the following month, though with less efficiency and a smaller volumetric expansion than secondary spheres. Attempts at propagating these after additional dissociation as quaternary spheres were generally unsuccessful. Given an apparent cell doubling time of 3-4 days, and monthly passages thus spanning 8-10 doublings, it was estimated that tertiary spheres assessed a month after last passage have undergone a minimum of 16-24 doublings, and no more than 30. This is well below the number of doublings of which tissue-derived stem cells are typically thought capable.

Figure 7:
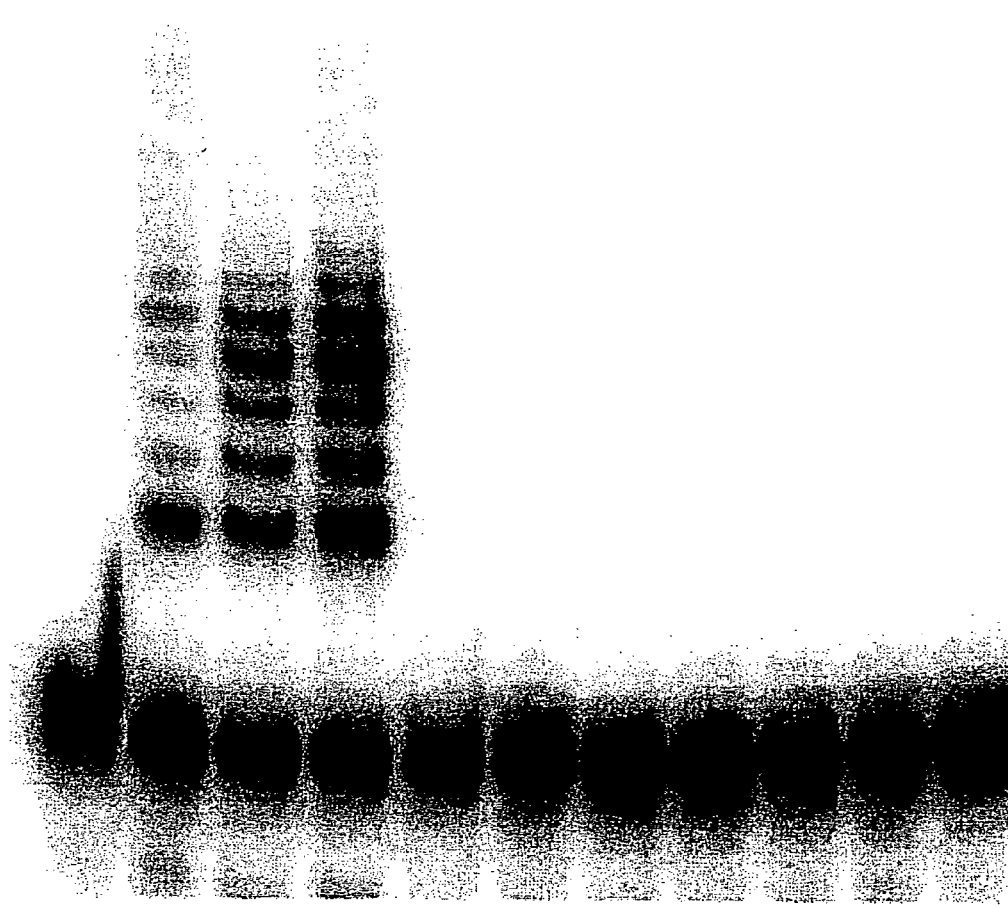
FIG. 7 shows WMPCs lack telomerase activity. Second passage spheres maintained in culture for three months were assessed for their telomerase activity using the TRAP assay. Lane 2 shows telomerase activity by 293 cells used as a positive control. Lanes 7, 9, and 11 show the absence of telomerase activity by matched WMPCs. Lanes 1, 6, 8, and 10 are heat inactivated controls of each sample. Lanes 3 and 4 are positive primer template controls, at concentrations of 0.1 M and 0.3 M. Methods: Telomerase activity was determined using the TRAP assay (Ostenfeld et al., "Human Neural Precursor Cells Express Low Levels of Telomerase in Vitro and Show Diminishing Cell Proliferation with Extensive Axonal Outgrowth Following Transplantation," *Exp Neurol*, 164:215-226 (2000); Kim et al., "Specific Association of Human Telomerase Activity with Immortal Cells and Cancer, *Science*, 266:2011-2015 (1994), which are hereby incorporated by reference in their entirety). Cells were solubilized in 100 μl of CHAPS lysis buffer, and 500 ng of protein assayed. For controls, cell lysates were preincubated at 85° C. for 10 min to inactivate telomerase. The samples were added to a mixture of TRAP buffer, dNTP, Taq polymerase (Promega), $^{32}$P-end-labeled TS primer (5'-AATCCGTCGAGCA-GAGTT-3' (SEQ ID NO: 1), reverse primer (Intergen, Gaithersburg, Md.), and T4 gene-32 protein (Boehringer Mannheim, Ind.). To test assay specificity, 0.5 μg/50 μl DNase-free RNase A (Promega), heat-inactivated at 65° C. for 20 min, was added to the reaction mixture. After a 30 min incubation at 30° C. for telomerase-mediated extension of the TS primer, the samples were amplified by PCR, and the products run on a 12.5% non-denaturing PAGE gel, then autoradiographed.

The inability to meaningfully passage these cells beyond the range of their 16-24$^{th}$ doublings called into question their ability to self-replicate for extended periods of time in vitro. Their limited replicative competence contrasted to that of neural progenitors sorted from the fetal human ventricular zone, which may be readily passaged for >60 doublings under analogous culture conditions (Keyoung et al., "Specific Identification, Selection and Extraction of Neural Stem Cells from the Fetal Human Brain," *Nature Biotechnology*, 19:843-850 (2001), which is hereby incorporated by reference in its entirety). Such self-renewal capacity has been ascribed to sustained telomerase activity in a number of developing systems, including the fetal human forebrain (Yashima et al., "Expression of the RNA Component of Telomerase During Human Development and Differentiation," *Cell Growth Differ.*, 9:805-813 (1998); Ostenfeld et al., "Human Neural Precursor Cells Express Low Levels of Telomerase in Vitro and Show Diminishing Cell Proliferation with Extensive Axonal Outgrowth Following Transplantation," *Exp Neurol*, 164:215-226 (2000), which are hereby incorporated by reference in their entirety). To determine if the apparently finite proliferative potential of adult human WMPCs cells reflected a lack of telomerase activity, telomerase levels were assessed using the telomerase reverse transcriptase activity protocol (TRAP) assay (Ostenfeld et al., "Human Neural Precursor Cells Express Low Levels of Telomerase in Vitro and Show Diminishing Cell Proliferation with Extensive Axonal Outgrowth Following Transplantation," *Exp Neurol*, 164:215-226 (2000); Kim et al., "Specific Association of Human Telomerase Activity with Immortal Cells and Cancer, *Science*, 266:2011-2015 (1994), which are hereby incorporated by reference in their entirety). No telomerase activity was detected in either primary or secondary WMPC-derived spheres, despite high-level activity detected in a variety of positive controls (FIG. 7). The lack of extended replicative potential, coupled with their lack of telomerase activity, suggests that adult WMPCs might constitute a pool of multipotential progenitors with a finite capacity for mitotic expansion, transitional between tissue-restricted stem cells and phenotypically-committed progenitors.

Example 19

WMPCs Produced Neurons as Well as Glia Upon Fetal Xenograft

It was next asked if WMPCs were multipotential in vivo as well as in vitro. To this end, their fate upon engraftment to E17 fetal rat brains was evaluated. Some A2B5-sorted cells were transplanted within 24-48 hrs post-sort, to assess their lineage potential upon initial isolation. These cells were maintained only in SFM during the period in between isolation and xenograft, and were never exposed to any exogenous growth factors. Others were transplanted 10 days after sorting, after maintenance in bFGF/NT3/PDGF-AA (4 days) and 15% serum/PDGF-AA and bFGF (6 days). All donor cells were injected at $10^5$ cells/animal, into E17 rat embryos via intraventricular injection. The recipients were sacrificed and fixed 4 weeks after birth, so as to evaluate the fate of the implanted human cells. Their brains were removed and cut at 15 μm, and the human donor cells identified by immunolabeling for human nuclear antigen (hNA).

In both sets of rats, those implanted with propagated WMPCs (FIG. 6) and their counterparts injected with acutely-isolated WMPCs (FIG. 8), hNA/βIII-tubulin+ neurons were found in the forebrain subependyma, including the rostral migratory stream and olfactory subependyma (FIGS. 6A-B), as well as in the hippocampal alvius (FIG. 6E). Migrants expressing hNA together with either nestin or doublecortin (Gleeson et al., "Doublecortin is a Microtubule-Associated Protein and is Expressed Widely by Migrating Neurons," *Neuron*, 23:257-271 (1999), which is hereby incorporated by reference in its entirety) were similarly found in the host olfactory subependyma and hippocampus (FIG. 6D). These data demonstrated that adult human WMPCs can integrate into the neurogenic anterior subventricular zone as neuronal progenitor cells. In addition, WMPC-derived neurons were noted in the neostriatum as well, indicating striatal neuronal differentiation on the part of some xenografted WMPCs (FIG. 6F). Human WMPC-derived GFAP+ astrocytes and CNP+ oligodendrocytes were also common in the recipient brains and were found primarily along the ventricles or in the subcortical white matter. Thus, adult human WMPCs exhibited context-dependent differentiation following xenograft to the developing rat brain, and were competent to do so upon their acute isolation, without benefit of humoral instruction in vitro.

These observations suggest that the WMPCs of the adult human forebrain include multipotential progenitor cells, capable of a finite and limited degree of expansion and self-renewal. These cells remain competent to respond to local instructive cues with a wide range of lineage choices, upon xenograft as well as in vitro. They are readily able to give rise to neurons as well as glia, once removed from their native white matter environment. As such, freshly isolated adult WMPCs required no prolonged expansion in order to exhibit neurogenesis in vitro, and appeared immediately competent to generate neurons upon xenograft to the developing brain.

Previous studies of the adult rat brain have identified parenchymal progenitor cells, that become able to give rise to neurons as well as glia after a number of cell doublings in the presence of bFGF (Palmer et al., "Fibroblast Growth Factor-2 Activates a Latent Neurogenic Program in Neural Stem Cells from Diverse Regions of the Adult CNS," *J Neurosci,* 19:8487-8497 (1999), which is hereby incorporated by reference in its entirety). In addition, nominally committed glial progenitor cells derived from the neonatal rat optic nerve have also been reported to give rise to neurons as well as oligodendrocytes (Kondo et al., "Oligodendrocyte Precursor Cells Reprogrammed to Become Multipotential CNS Stem Cells," *Science,* 289:1754-1757 (2000), which is hereby incorporated by reference in its entirety). The lineage diversification of these cells appeared to require a humorally-directed reprogramming of phenotype, with the induction of an astrocytic intermediary on the way to neurogenesis. In the present study, adult human WMPCs cells did not appear to require any such reprogramming or transdifferentiation to achieve multilineage competence. Similarly, they did not appear to require any traversal through an intermediate astrocytic stage in order to generate neurons, oligodendrocytes, and astrocytes. Indeed, upon their acute isolation and xenograft, A2B5-defined WMPCs were able to generate all major neural phenotypes in vivo as well as in vitro, without any benefit of exogenous growth factor exposure. Nonetheless, since an average of 7% of A2B5-sorted white matter cells co-expressed GFAP, it is possible that some WMPCs exhibit astroglial features at some point during their ontogeny, much as do subventricular neural progenitor cells (Doetsch et al., Subventricular Zone Astrocytes are Neural Stem Cells in the Adult Mammalian Brain," *Cell,* 97:703-716 (1999); Alvarez-Buylla et al., "Neurogenesis in Adult Subventricular Zone," *J Neurosci,* 22:629-634 (2002), which are hereby incorporated in their entirety). Their categorization notwithstanding, the results suggest that the WMPC of the adult human brain is fundamentally a tissue-specific progenitor cell, which is tonically restricted to glial lineage by the local parenchymal environment, and does not require specific phenotypic reprogramming for neuronal differentiation.

These data suggest that adult human WMPCs constitute a population of parenchymal glial progenitor cells, whose in situ fate is restricted by the local white matter environment. Yet the progenitor cell pool of the adult white matter may be heterogeneous, and it is by no means clear whether all WMPCs enjoy the same ontogeny or fate potential (Kukekov et al., *Glia,* 21:399-407 (1997); Levine et al., "The Oligodendrocyte Precursor Cell in Health and Disease," *Trends Neurosci,* 24:39-47 (2001); Mason et al., "*J. Molec. Cell. Neurosci.,* 20:30-42 (2002), which are hereby incorporated by reference in their entirety). A minority of multipotential progenitor cells might still persist among a larger pool of more fundamentally lineage-restricted glial progenitors (Palmer et al., "Fibroblast Growth Factor-2 Activates a Latent Neurogenic Program in Neural Stem Cells from Diverse Regions of the Adult CNS," *J Neurosci,* 19:8487-8497 (1999), which is hereby incorporated by reference in its entirety). Indeed, the parenchymal multipotent progenitor may yet constitute a relatively rare subpopulation, more akin to a persistent stem cell than to any lineage-restricted derivative (Jiang et al., "Pluripotency of Mesenchymal Stem Cells Derived from Adult Marrow," *Nature,* 418:41-49 (2002); Capela et al., "LeX/ssea-1 is Expressed by Adult Mouse CNS Stem Cells, Identifying Them as Nonependymal," *Neuron,* 35:865-875 (2002), which are hereby incorporated by reference in their entirety). In this regard, although telomerase activity in sorted WMPCs was not detected, if the clonogenic portion thereof represents but a small fraction of the total progenitor pool, then their numbers might have been below the detection threshold of the TRAP assay. Clearly then, further study of the heterogeneity of the white matter progenitor cell population, and of the lineage competence of its constituent phenotypes, will be needed to define the spectrum of progenitor cell types in the adult brain. These considerations aside, multipotential and neurogenic progenitors are clearly abundant in the adult human white matter, and are both extractable and expandable. As such, these cells may prove important agents for both induction and implantation strategies of cell-based neurological therapy.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of producing neuronal progenitor cells comprising:
   dissecting primarily white matter from adult human brain tissue;
   isolating a population of neural progenitor cells from the dissected adult human brain tissue white matter, said isolating comprising immunoseparating the human white matter progenitor cells by extracting cells expressing immunoreactivity for A2B5;
   permitting the isolated population of neural progenitor cells from the dissected adult human brain tissue white matter to differentiate to neuronal progenitor cells, in the presence of one or more growth factors; and
   recovering an enriched population of neuronal progenitor cells after said permitting the isolated population of neural progenitor cells from the dissected adult human brain tissue white matter to differentiate to neuronal progenitor cells.

2. The method according to claim 1, wherein the one or more growth factors are selected from the group consisting of basic fibroblast growth factor, platelet-derived growth factor, neurotrophin-3, and combinations thereof.

3. The method according to claim 1, wherein said immunoseparating is carried out with a fluorescently labeled antibody which recognizes the A2B5 antigen on the human white matter progenitor cells.

4. The method according to claim 3, wherein said immunoseparating human white matter progenitor cells further comprises:
   fluorescence activated cell sorting.

5. The method of claim 1, wherein said dissecting is carried out so that the dissected white matter is free of adjacent cortex and epithelium.

* * * * *

SEQUENCE LISTING

<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 1
aatccgtcga gcagagtt                                                  18